(12) United States Patent
Holupka et al.

(10) Patent No.: US 6,256,529 B1
(45) Date of Patent: Jul. 3, 2001

(54) VIRTUAL REALITY 3D VISUALIZATION FOR SURGICAL PROCEDURES

(75) Inventors: Edward J. Holupka, Medway, MA (US); Everette C. Burdette, Champaign, IL (US); Irving D. Kaplan, Newton, MA (US)

(73) Assignee: Burdette Medical Systems, Inc., Champaign, IL (US)

( * ) Notice: Subject to any disclaimer, the term of this patent is extended or adjusted under 35 U.S.C. 154(b) by 0 days.

(21) Appl. No.: 08/977,362

(22) Filed: Nov. 24, 1997

Related U.S. Application Data

(63) Continuation-in-part of application No. 09/150,452, filed on Sep. 9, 1998, now Pat. No. 6,208,883, which is a continuation of application No. 08/507,199, filed on Jul. 26, 1995, now Pat. No. 5,810,007.

(51) Int. Cl.[7] ........................................................ A61B 6/00
(52) U.S. Cl. ............................................ 600/427; 600/439
(58) Field of Search .................................. 600/427, 407, 600/411, 439, 7, 459; 348/7; 128/920, 922, 916

(56) References Cited

U.S. PATENT DOCUMENTS

| | | | |
|---|---|---|---|
| 5,391,139 | * | 2/1995 | Edmundson . |
| 5,526,812 | * | 6/1996 | Dumoulin et al. . |
| 5,765,561 | * | 6/1998 | Chen et al. . |
| 5,810,007 | * | 9/1998 | Holupka et al. . |
| 5,817,022 | * | 10/1998 | Vesely . |
| 5,868,673 | * | 2/1999 | Vesely .................................. 600/407 |
| 5,871,448 | * | 2/1999 | Ellard . |
| 5,931,786 | * | 8/1999 | Whitmore, III et al. . |
| 5,951,571 | * | 9/1999 | Audette ................................ 606/130 |
| 6,006,126 | * | 12/1999 | Cosman ................................ 600/426 |
| 6,027,446 | * | 2/2000 | Pathak et al. ......................... 600/439 |
| 6,038,467 | * | 3/2000 | De Bliek et al. . |
| 6,048,312 | * | 4/2000 | Ishrak et al. ......................... 600/443 |
| 6,083,166 | * | 7/2000 | Holdaway et al. ................... 600/439 |
| 6,095,975 | * | 8/2000 | Silvern ................................. 600/439 |
| 6,129,670 | * | 10/2000 | Burdette et al. ..................... 600/427 |

\* cited by examiner

Primary Examiner—Marvin M. Lateef
Assistant Examiner—Shawna J Shaw
(74) Attorney, Agent, or Firm—Michael D. Rechtin; Foley & Lardner

(57) ABSTRACT

A method and apparatus for three-dimensional imaging and treatment of a patient's body. The method and apparatus utilize a system for developing a therapy plan for treatment of an organ of the patient, a device for generating ultrasound image data from a treatment region and a device for providing a translucent volume image of a portion of a patient's body and a separate translucent image of the patient organ and a three dimensional viewing device to superimpose a translucent article image to enable viewing of the article image simultaneously with the patient organ and a portion of the patient's body.

54 Claims, 11 Drawing Sheets

VIRTUAL REALITY 3D VISUALIZATION FOR SURGICAL PROCEDURES

This is a continuation-in-part of an application filed Sep. 9, 1998 having Ser. No. 09/150,452 (now U.S. Pat. No. 6,208,883) which is a continuation of Ser. No. 08/507,199 (now U.S. Pat. No. 5,810,007) filed Jul. 26, 1995.

The present invention is directed in general to an improved method and apparatus for carrying out minimally invasive treatments of the human body by virtual reality visualization of the treatment area. More particularly the invention is concerned with use of a three-dimensional ("3D") imaging probe apparatus and method for providing a real time, 3D, ultrasound, translucent rendering of a human anatomy undergoing treatment along with real time translucent rendering of treatment devices interacting with the organ. Such a methodology would be particularly useful as a system for guidance of minimally invasive surgical instruments within tissues to be treated as well as for deposition of radioactive seeds, or placement of other radioactive sources, and for radiotherapy of cancerous tissues in a human organ, such as the male prostate.

New minimally invasive surgical procedures are most often optically guided, but such optical guidance methods do not permit visualization and guidance of instruments or probes within (inside) the target tissue or organ. Incorporation of real-time 3D visualization inside diseased tissues would provide accurate guidance of therapy. Open-magnet MRI is used to visualize some procedures such as thermal therapy and brain biopsies. However, the method is expensive, not truly real-time, and is limited in application.

Numerous conventional treatment methods involve attempts to provide a targeted dosage of radiation or chemicals to the organ, and such treatments are often based on general anatomical assumptions of size and location. These methods suffer from inaccuracy of localizing the target for any one particular individual and potential real time changes of relative orientation and position of target tissue, normal tissue, and radiation therapy devices.

It is instructive in explaining the invention to consider one specific type of exemplary condition, adenocarcinoma of the male prostate which is the most commonly diagnosed cancer in the male population of the United States. At present, 254,000 new cases of prostate cancer were diagnosed in 1995 and 317,000 in 1996. In the 1960s, a method of implanting radioactive gold or iodine seeds was developed. With this approach, the radioactive material is permanently placed into the prostate via a retropubic approach during laparotomy when diagnostic lymphadenectomy was also being performed. A high dose of radiation is delivered to the prostate as the radioactive seeds decay. In several reports, the five year disease free survival ("local control") obtained by this method was compared to similarly staged patients treated with an external radiation beam. In view of this, gold was replaced by $I^{125}$ implantation for safety of personnel doing implantation. Except for early stage prostate cancer (T2a tumors), inferior rates of local control are reported with "free hand" 125-Iodine implantation. There was significant dose inhomogeneity due to the nonuniformity of seed placement, leading to underdosing of portions of the prostate gland and significant complications due to overdosing of adjacent healthy tissue structures. The poor results for local control and normal tissue complication were attributed to the doctor's inability to visualize and hence control where the radioactive seeds were actually being deposited inside the patient.

Recently, transrectal ultrasonography ("TRUS") has been used to visualize 125-Iodine seed placement during transperineal implantation. The early reported rates of serious late complications is higher than external beam therapy. Even with this technique, significant imprecisions in seed placement are observed. Due to the proximity of the prostate to the rectum and bladder, incorrect seed placement may lead to serious overdosing of these structures and late complications.

The recent transrectal ultrasound guided transperineal implant technique has been developed which is in use. That procedure is described in three steps: (1) the initial volumetric assessment of the prostate gland performed using ultrasound, (2) development of a radiation therapy "pre-plan," and (3) performing the actual intraoperative implant. The purpose of the initial volumetric assessment prior to the pre-plan or implantation is to obtain a quantitative understanding of the size of the prostate, which is then used to determine the total activity and distribution of radioactivity which is to be implanted into the prostate. To perform the assessment, an ultrasound probe is physically attached to a template. The template is a plastic rectangle which contains an array of holes separated at predefined intervals, usually 5 mm. The template system serves two purposes: (1) to fix the ultrasound probe, and hence the imaging plane to the reference frame of the catheter and seed positions, and (2) to guide the catheters into the prostate volume. More specifically, the template system serves as a reference frame for spatial quantities which are required for the description of the implant procedure. Using transrectal ultrasound, a number of serial ultrasound images are obtained at 5-mm intervals, and the prostate is outlined on each image. The images are taken so that the entire prostate gland is covered. This results in a stack of two-dimensional ("2D") outlines, or contours, which, taken together, outline the entire 3D prostate volume. From this volume, the quantitative volume of the prostate is calculated.

Once the 3D contour data has been obtained for the prostate volume, a radiation therapy plan which describes the positions of the radioactive seeds within the prostate is developed. This plan attempts to optimize the dose to the prostate, minimize the dose to surrounding healthy tissue, and minimize dose inhomogeneity. The positions of the radioactive seeds are constrained to fall within the catheter tracks, since the seeds are placed within the prostate transperineally via these catheters. The result of the pre-plan describes the positions and strengths of the radioactive seeds within the catheter which optimizes the dose to the prostate.

Intraoperatively, the TRUS probe is inserted, and the template is mounted against the perineum. As previously described, the template is a plastic rectangle which contains an array of holes separated at fixed intervals. These holes act as guides for the catheters. The TRUS probe is inserted into the rectum and placed so that the image corresponds to the prostate base (the maximum depth). Two or three catheters are inserted into the tissue surrounding the prostate or in the periphery of the prostate to immobilize the gland. These catheters contain no radioactive seeds. This image serves as a spatial reference for all further images and seed positions within the prostate. Subsequently, catheters are inserted into the gland based on the pre-plan through the template. The ultrasound probe is positioned each time so that the catheter, and hence seeds, which are inserted into the prostate are visible on the ultrasound image. If the placement of the catheter within the prostate is not according to the pre-plan, the catheter is then withdrawn and reinserted until the catheter is correctly placed. This is a time-consuming process; and it is very difficult to achieve optimal placement. Invariably, the catheters deflect angularly as they are inserted, and their positions are difficult to determine by 2D ultrasound. This is due to the fact that the visualization process is a 2D process while the actual implant procedure is 3D. Once all the seeds are in place, another series of 2D images are obtained to quantify the final, resultant dose distribution delivered to the patient. In some instances, a pair of orthogonal fluoroscopic images are also obtained to determine the final seed placements. This procedure is usually performed a few weeks post implant.

These above described prior art systems suffer from inherent inaccuracy, the inability to correct the positioning of the radioactive seeds without repeated withdrawal and reinsertion of seeds into the prostate and are not real time manipulations of the therapeutic medium. Further, the overall positioning of the template and patient may be different during treatment compared to the assessment phase. Consequently, the catheter position and seed position may be at an undesired position relative to the presumed assessment phase location.

It is therefore an object of the invention to provide an improved system and method for invasive treatment of the human body.

It is another object of the invention to provide a novel system and method for real time and/or near real time, 3D visualization of a human organ undergoing invasive treatment.

It is also an object of the present invention to provide a more precise and accurate implant placement for radiation therapy, thermal therapy, and surgical ablation.

It is also an object of the invention to provide an improved system and method for generating a 3D image data set of a human organ for a treatment protocol using a real-time ultrasound imaging system with spatial landmarks to relate the image data set to present time, invasive treatment devices.

It is a further object of the invention to provide a novel system and method for mapping the 3D images of a human organ, such as the male prostate, and using these images as a translucent colored volume enabling projection of real-time 3D virtual images to a physician performing invasive treatment manifested by virtual images of the treatment devices within the field of the virtual images of the organ.

It is an additional object of the invention to provide an improved method and system for 3D virtual imaging of the male prostate gland and overlaid virtual imaging of devices being inserted into the prostate for deposition of radioactive seeds for cancer therapy.

These and other objects and advantages of the invention will be readily apparent from the following description of the preferred embodiments thereof, taken in conjunction with the accompanying drawings described below.

DETAILED DESCRIPTION OF PREFERRED EMBODIMENTS

Figure 1:
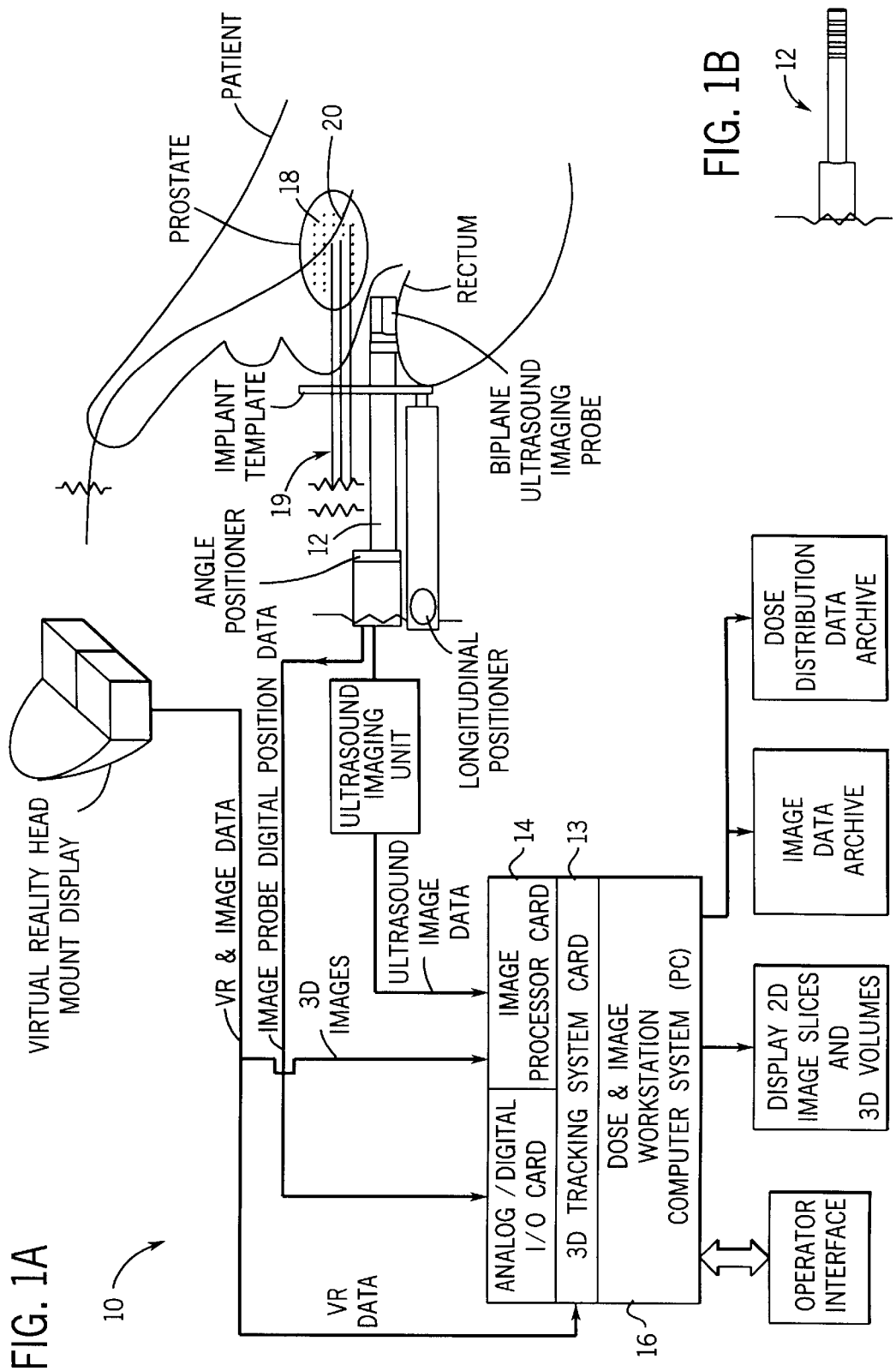
FIG. 1A illustrates a block diagram of an embodiment of the invention and FIG. 1B shows an alternate embodiment for a three-dimensional probe.

A system 10 constructed in accordance with an example of the invention is illustrated generally in FIG. 1. A three-dimensional (3D) probe 12 accumulates image data from a treatment region or organ of a patient, image data is processed using a 3D imaging card 14. The probe 12 preferably is an ultrasound device but can be any other rapid imaging technology, such as rapid CT or MR. A conventional personal computer 16 having a monitor can be used to operate on the image data from the imaging card 14 using conventional software and hardware tools to be described in more detail hereinafter. Radioactive seeds 18 are provided for insertion using any one of a variety of conventional means for inserting devices or articles into the human body, such as insertion devices 19, which may be either needles or stiff catheters. The 3D ultrasound probe 12, therefore, provides an image signal to the computer 16 and a virtual realty interface card 13 coupled to the imaging card 14 which enables a user to visualize a translucent image of the patient organ and real time interaction of any one of a variety of treatment devices, such as the implant needles 19 or a Foley catheter 20, and one of the seeds 18 within the organ. Computer software can be utilized in a conventional manner to visualize the 3D imaging data in various formats. The formats include orthogonal two dimensional (2D) images, oblique 2D images, and translucent 3D rendering. All of these reconstructions can be directly displayed on the computer monitor; and 3D translucent, stereoscopic, rendering is also available in the VR (Virtual Realty) mode.

The preferred ultrasound probe 12 is a conventional Kretz ultrasound imaging system manufactured by Kretz Corporation, now available as Medison Combison 530 through Medison America Corporation, Pleasantown, Calif. This system and other such conventional systems are readily available and can provide real time ultrasound image data. The Medison Combison ultrasound system incorporates an endorectal probe which acquires multiple image planes in real time and the software of the present invention reconstructs the translucent 3D volume. Alternate systems include bi-plane 2D imaging systems with the probe mounted in a stepper motor driven holder for rapid automatic acquisition of multiple image planes. There is nothing that is application specific about the imaging system, thus any commercially available system will suffice.

Figure 2:
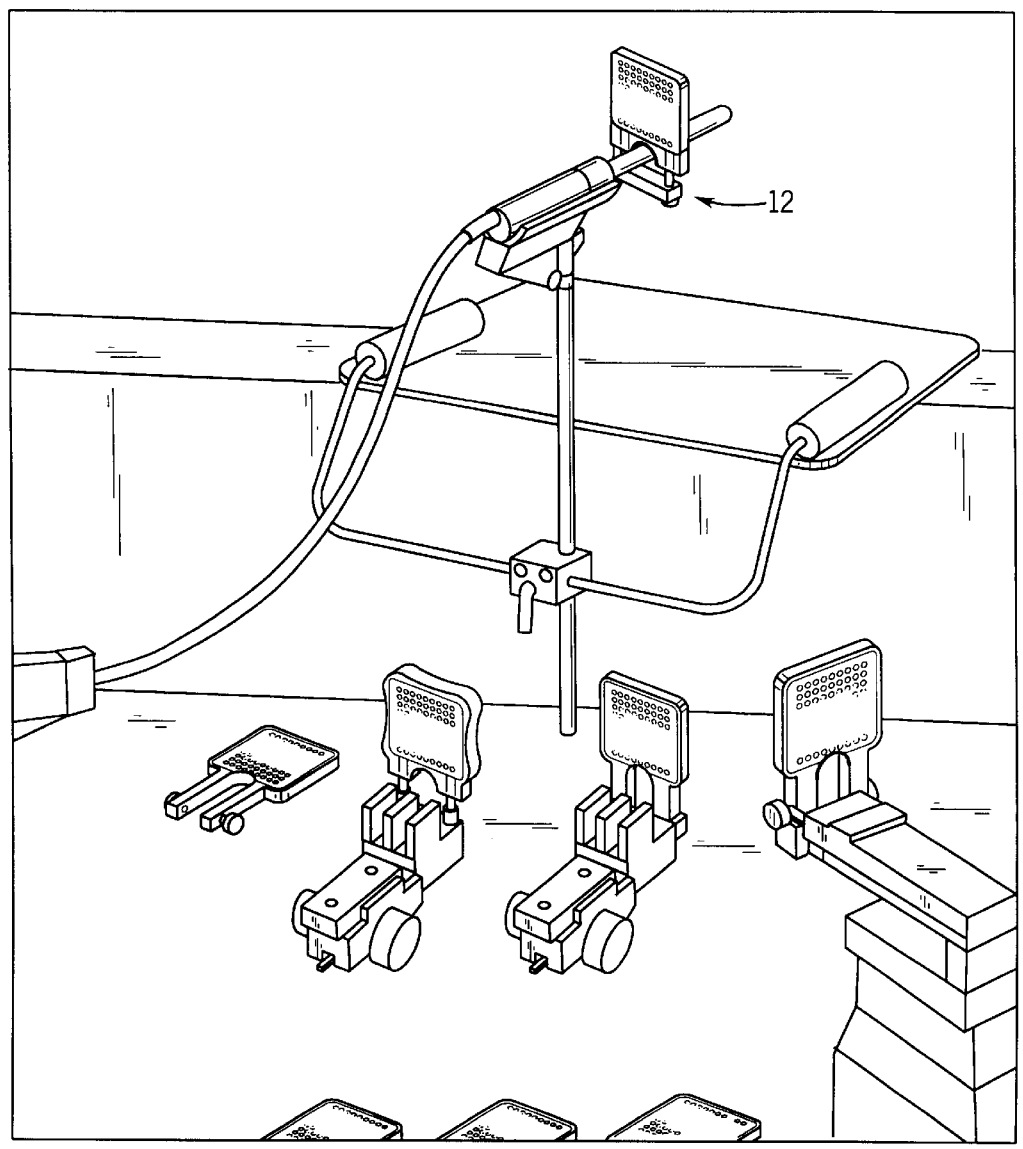
FIG. 2 illustrates an ultrasound guided implant system.

For collecting ultrasound image data, the diagnostic transrectal ultrasound probe 12 (see FIG. 2) is inserted into the patient's rectum to obtain real time volumetric images of the prostate for use during the implant procedure. The diagnostic probe 12 is preferably a phased array probe designed so that the array of transducers can rotate about the axis of the array sweeping out a 3D imaging volume. As the probe 12 rotates, images are captured and digitized by use of the imaging card 14 (see FIG. 1), so as to create a fixed number of images slices per rotation. An alternative method utilizes a transverse oriented phased array form of the endorectal probe 12 which is moved longitudinally in an automated rapid sequence so as to create a series of transverse image slices automatically. Another embodiment of the probe 12 can incorporate multiple transverse phased arrays (shown in phantom in FIG. 1B) arranged parallel to each other orthogonal to the axis of an endorectal probe to produce multiple simultaneous image slices (see, for example, FIGS. 5A and 5B). The 3D image data will be represented as a three dimensional image raster.

Figure 3A:
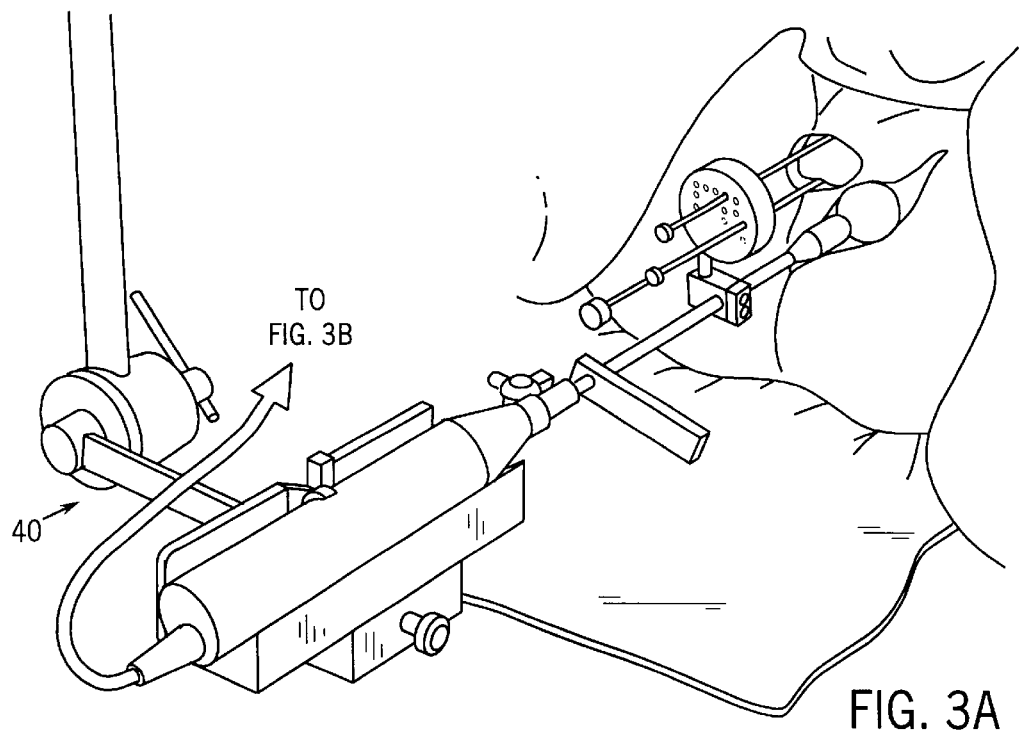
FIG. 3A illustrates patient setup for a radioactive implant procedure.
Figure 3B:
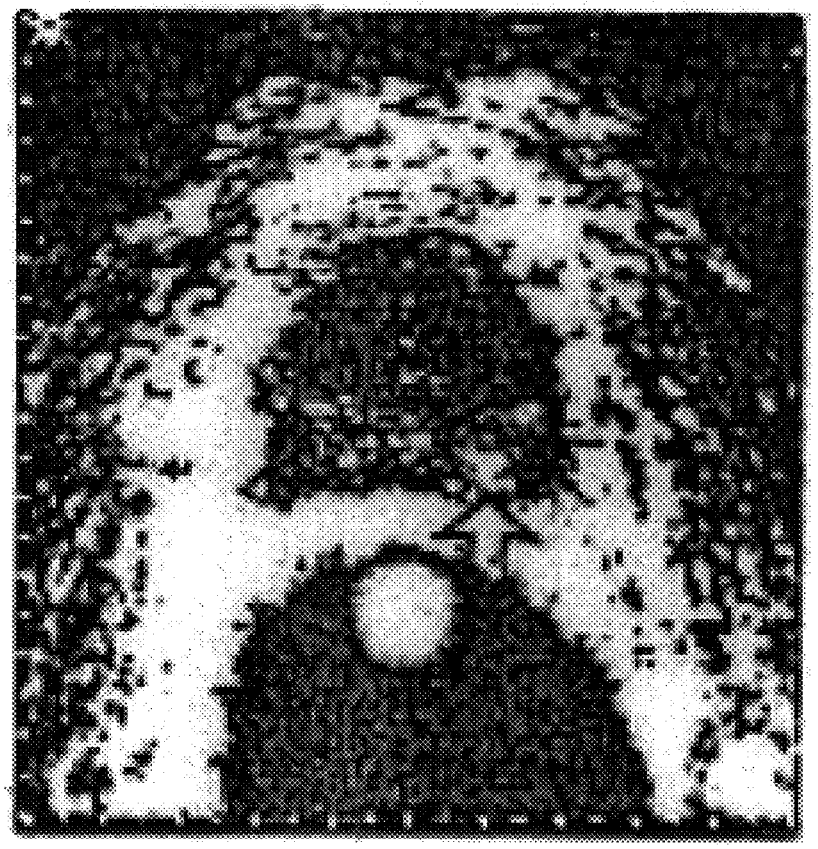
FIG. 3B illustrates an anatomical prostate phantom used for testing and planning.
Figure 3C:
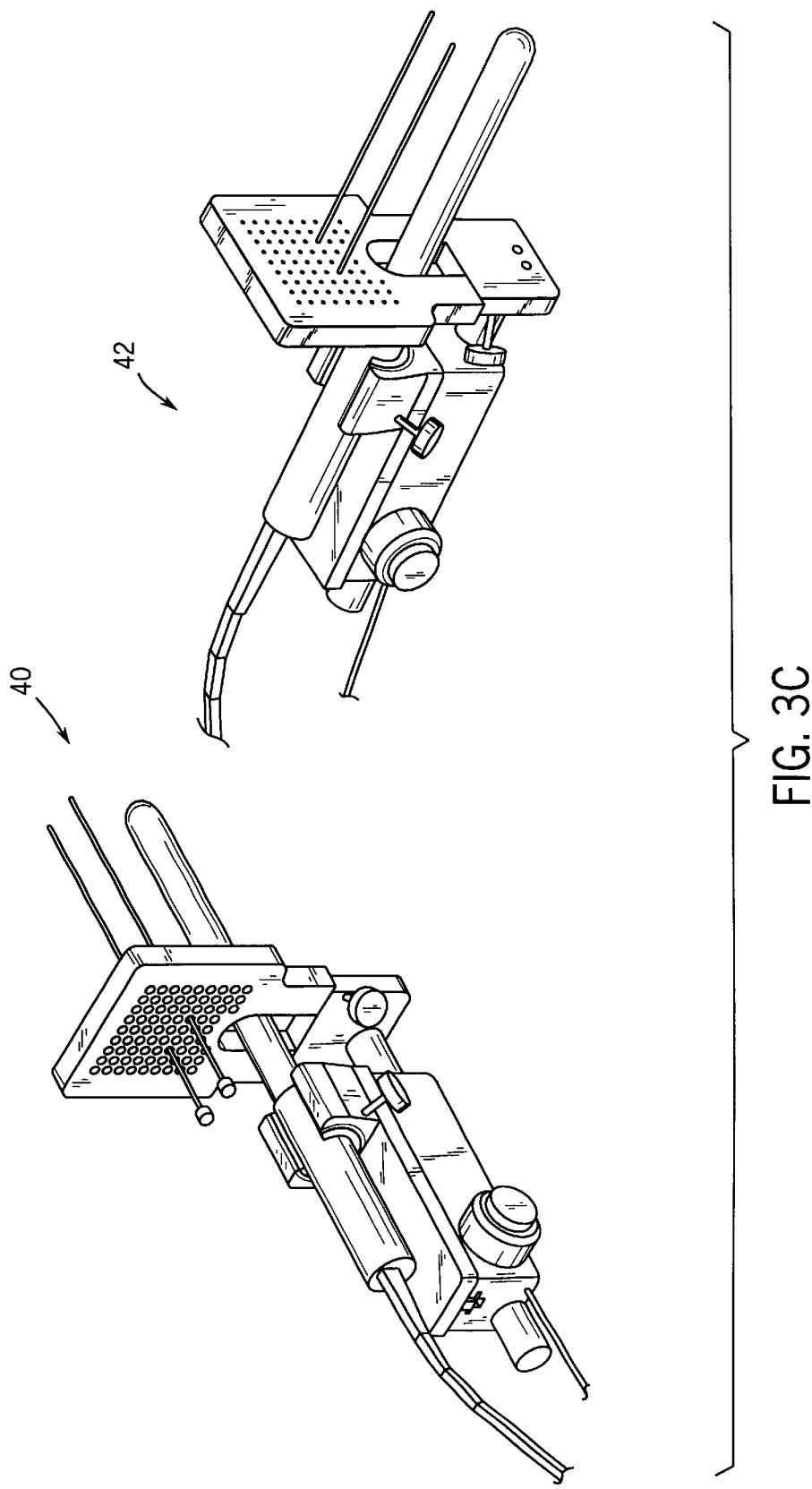
FIG. 3C illustrates in detail a probe holder/stepper assembly shown partly in FIG. 3A.
Figure 4A:
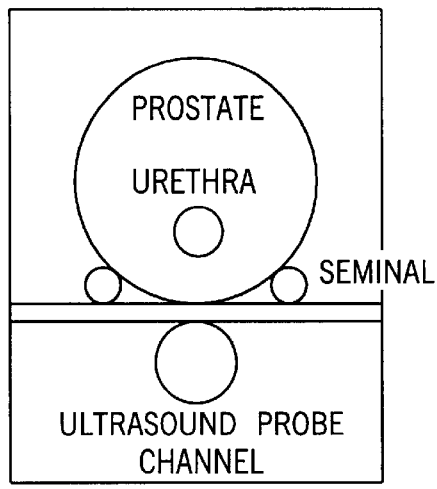
FIG. 4A illustrates a front schematic view of a brachytherapy phantom and FIG. 4B a side schematic view of the brachytherapy phantom.
Figure 4B:
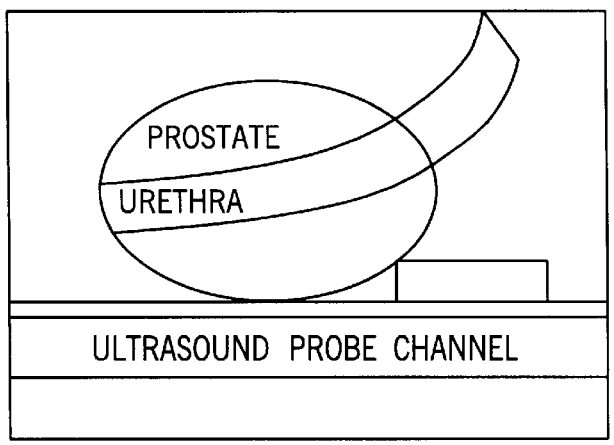

The ultrasound probe 12 can be mounted into a probe holder 30 (see FIGS. 3A and 3C) with FIG. 3B illustrating one example of an ultrasound image from an anatomical prostate phantom employed to carry out testing and planning. The probe holder 30 includes a digital encoder 42 for providing information regarding the position of all of the desired ultrasound image planes in the prostate relative to each other. The image plane location will be automatically sent to the system computer and "tagged" to the acquired ultrasound image for that position. Thus, it will be possible to reproduce the longitudinal and lateral positions of the implant catheters for the ultrasound therapy applicators and for the temperature probes.

There are several possible image processing cards which could be utilized; however, using current modalities each of the processing cards is configured specifically for 3D. The 3D image raster is buffered; and thus, for example, if the 2D images are 512×512 and there are sixteen image planes in the probe 12, and each pixel is a byte (256 gray scales), at least a 512×512×16 byte=4.2 Mbyte image buffer in the card 14 is needed. Several commercial cards (for example, made by Coreco, Matrox and Integral Technologies) can be equipped with this amount of video RAM (VRAM), but the way the card's hardware interacts with the computer's video and software drivers does not utilize this data in 3D. Current available methodologies enable augmenting the software and some hardware of these cards so that they can act as a 3D card. The processing and memory architecture preferably is designed to allow for simultaneous image acquisition and processing. The digitizing card should also preferably have standard imaging tools, such as real time window and leveling, zoom and pan of the ultrasound images. Some existing cards (e.g., Matrox; Coreco) do provide standard imaging tools.

The 3D image data arising from the ultrasound probe 12 is preferably buffered on the imaging card 14. The 3D image is preferably represented as a series of 2D images. This is referred to as the image stack or 3D image raster. The 3D image raster is represented in memory as a linear array of bytes of length N×M×P where N is the width of the 2D image in pixels, M is the height a 2D image in pixels, and P is the number of 2D images in the image stack.

In a preferred embodiment the user can include defined formats. Entire 3D image stacks at specific times during the intraoperative session can be stored in the DICOM standard. The user will have the ability to select a 3D image volume for archiving as part of the system software. These image stacks can then be reviewed in any of the various visualization modes (standard orthogonal 2D views, oblique 2D views, or 3D translucent views) as described above. In addition, the user will have the ability to store any of the 2D views available at any time during the intraoperative session.

The computational platform can, for example, be any form of computing means, such as the personal computer 16, which incorporates a PCI bus architecture. Currently, PCI bus is preferable over the ISA or EISA bus because the PCI bus is much faster. However, a generic system which will be suitable for this applicable will be described. A 200 Mhz (or greater speed) Pentium/Pentium-Pro computer supplied with 128 Mbytes of RAM and a 6.0 Gbyte hard disk should be sufficient RAM and disk memory to run the software in a real-time fashion and to archive all patient data. There should be sufficient RAM to facilitate host image processing in parallel with onboard image processing for quality assurance checks. A high resolution monitor capable of displaying at least 1280×1024×64 bit resolutions is preferably used.

Based on currently available technology, the ultrasound images obtained from the ultrasound imaging system of the ultrasound probe 12 can be of good diagnostic quality. When transforming this input image data into a 3D representation, whether in the 3D perspective mode or the real time VR mode, the resultant volumes can, however, be noisy and hinder diagnostic and spatial accuracy. In order to improve the image quality, a number of conventional hardware and software filters can be used which will filter the incoming image data stored on the imaging card 14. Routines such as image pixel averaging, smoothing, and interpolation can improve the 3D rendering of the imaging volume. These sets of filters or routines are to be distinguished from the set of standard imaging tools running on the host CPU which are available within a conventional imaging software package.

Figure 6:
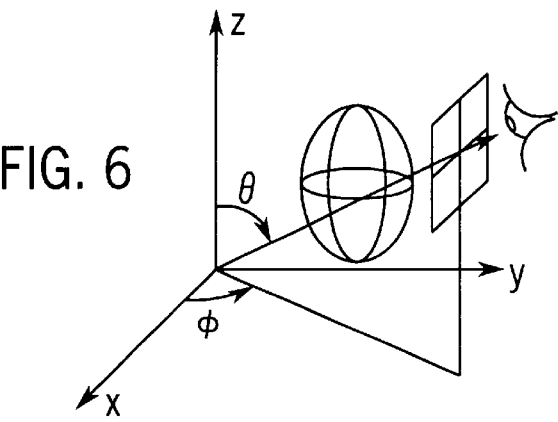
FIG. 6 illustrates the viewing geometry for a 3D translucent reconstruction of an image.
Figure 5A:
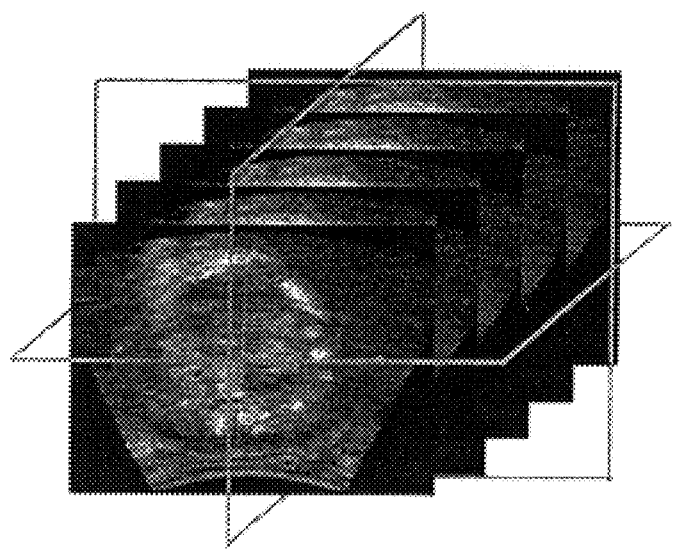
FIG. 5A illustrates reconstruction of standard orthogonal image planes from a 3D image stack and FIG. 5B the reconstruction of oblique image planes from a 3D image stack.
Figure 5B:
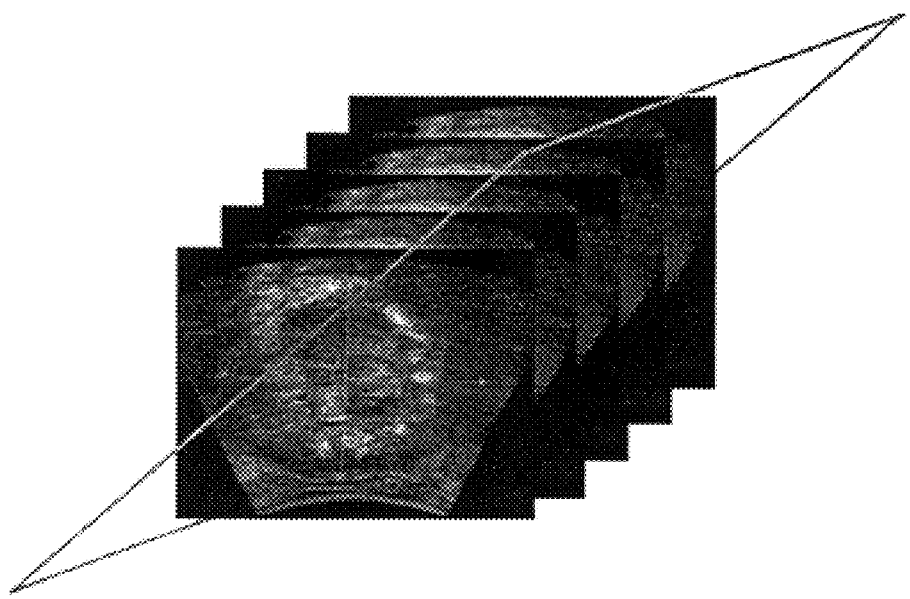
Figure 7A:
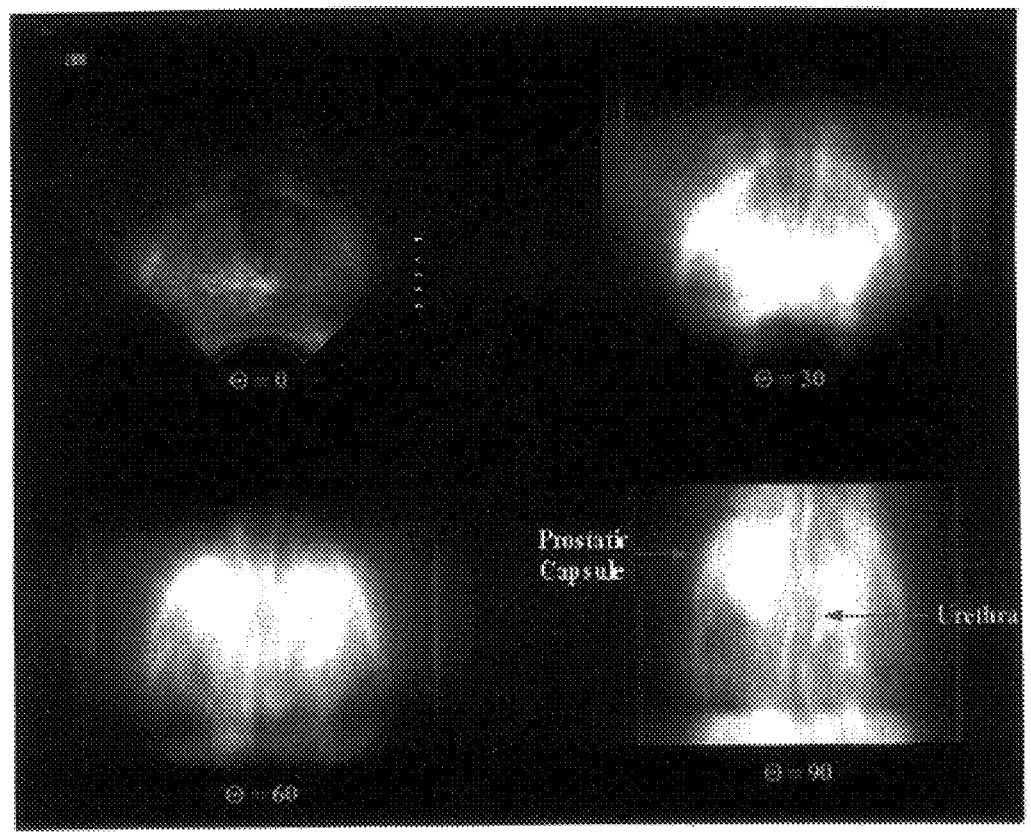
FIG. 7A illustrates translucent images of a human prostate for four different viewing angles and FIG. 7B illustrates translucent images of a phantom organ for six different viewing angles.
Figure 7B:
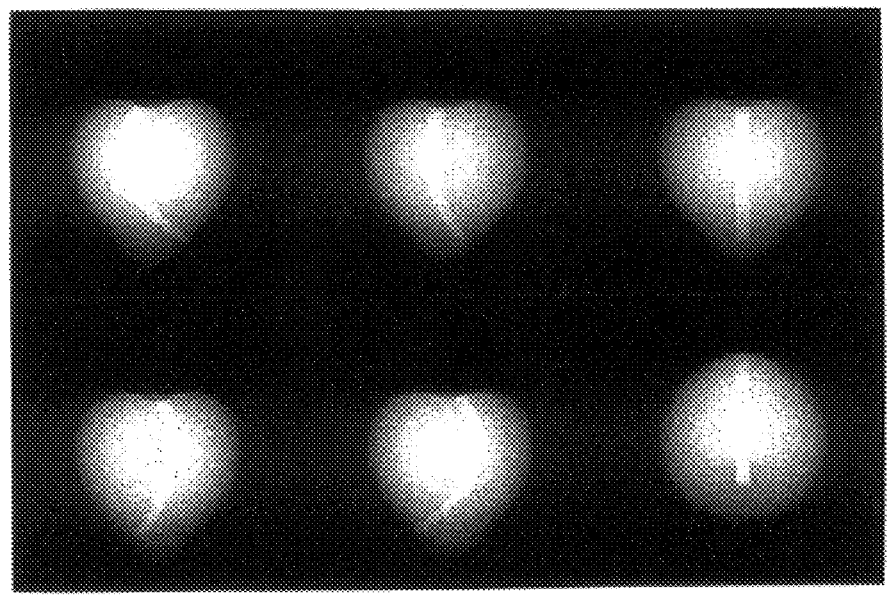

In the preferred embodiment, three of the perspective views are the standard transverse, coronal and sagittal 2D views. These three orthogonal views are taken from a user specified location within the imaging space. For example, the user can request that the three orthogonal views have their common centers at a spatial position of (5.0 cm, 15.0, 25.0 cm) relative to the origin of the template system. One also can select the reference point of either of the three orthogonal views independently, that is the three views do not have to have common center points. As mentioned hereinbefore, FIGS. 5A and 5B show examples of several example 2D views from a 3D ultrasound image volume. FIG. 6 shows a number of possible viewing directions, and FIG. 7 gives further examples of translucent 3D viewing from different angles. The 3D ultrasound image volume was obtained from actual ultrasound images of a human prostate and of a prostate implant phantom.

On each of the views, one can define, draw and edit contours using conventional computer software, such as Microsoft Foundation Class (MFC) view files. Each contour can be given a unique name by the user, and then drawn by the user using the mouse of the computer 16. All attributes of the contours such as name and color can, based on conventional imaging software, be user selectable. The user can also edit the contours by selecting functions, such as adding a point to a contour, deleting a point from a contour or deleting the entire contour. Once the contours are defined, the user has the option to render them in 3D or view in conventional 2D mode on the 3D perspective mode or viewed in the VR mode. Again, all contour 3D attributes such as color, lighting, and shading are user controlled. The contours by default appear on the 2D images, however, the user can control the individual contour's 2D and 3D visibility.

Figure 8:
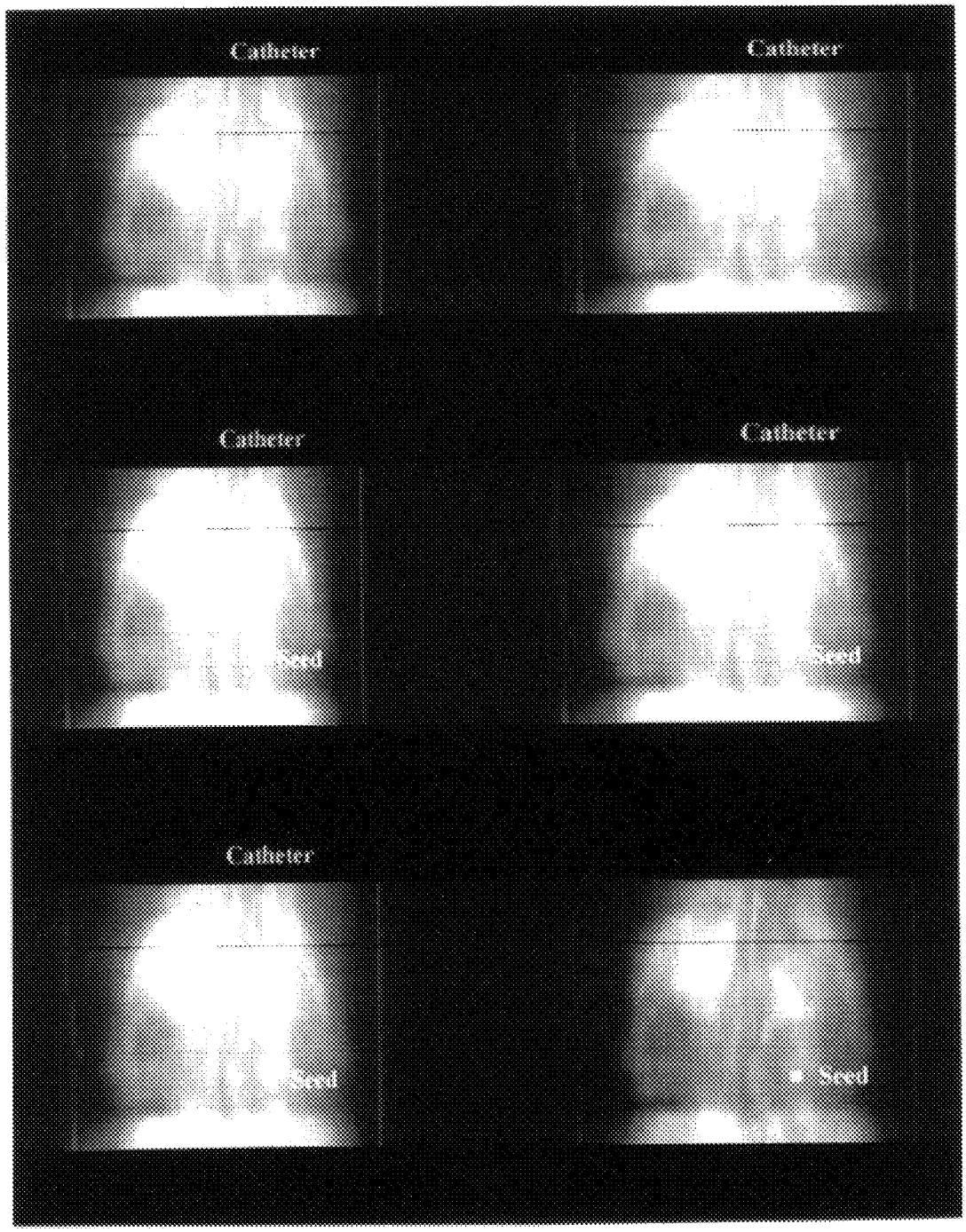
FIG. 8 illustrates a time sequenced image of the prostate organ in FIG. 7A showing approach of a catheter containing a radioactive seed, deposition of the seed and withdrawal of the catheter leaving the seed.
Figure 9:
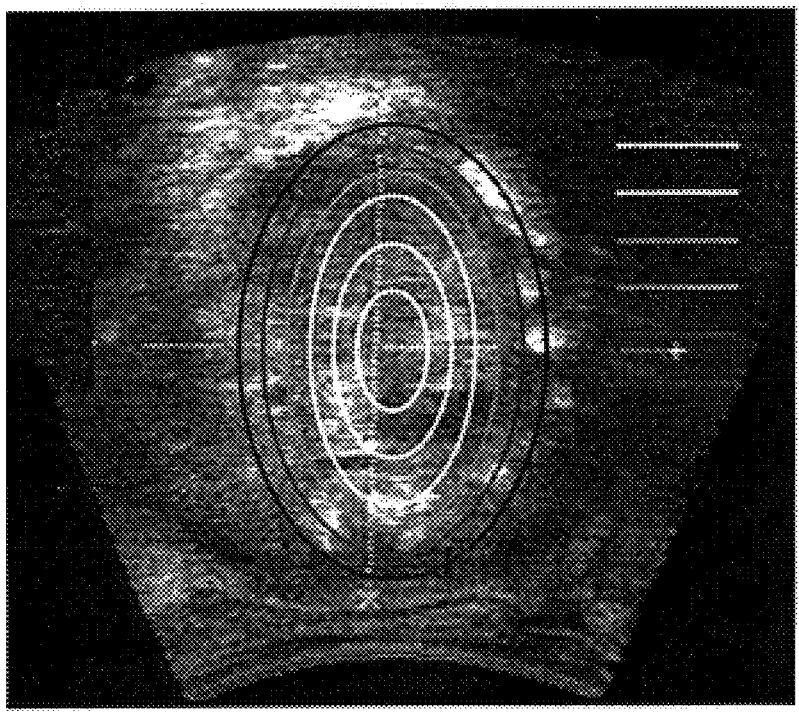
FIG. 9 illustrates isodose distributions of radiation from a single radioactive seed.

In order to improve the ability to visualize the real time, 3D information, the 3D image raster can be rendered as a real time, transparent, 3D volume. This transparent volume can be viewed and displayed on the monitor of the computer 16 at any arbitrary viewing angle and is calculated using conventional 3D object reconstruction algorithms. Such standard algorithms can render a large imaging volume in fractions of a second, even on present day computing platforms. The transparent nature of the reconstruction thus allows the user to "see" inside any objects which appear in the imaging volume. For example, if the prostate is imaged in the imaging volume, then it will be reconstructed as a transparent volume, in which other anatomical landmarks such as the urethra, tissue abnormalities or calcifications can be seen. In addition, if any other objects such as needles or catheters are inserted into the prostate, and if they are visible in the ultrasound images, they will be seen as they enter the prostate (see FIG. 8 showing introduction of the seed 18 with the catheter/needle 19). Since the volumes are rendered as transparent solids, the needles 19 (and other articles) can thus easily be seen as they move inside the prostate volume as well. Since the ultrasound images are obtained in real time, the 3D perspective reconstruction is also rendered in real time. The preferred algorithm for the perspective 3D reconstruction is the known Bresenham raytrace algorithm.

As described above, in the routine process of brachytherapy planning, the patient undergoes an initial volumetric ultrasound scan using the probe 12. This scan is done before the radiation therapy planning or the actual implant. During the radiation therapy planning, the ideal positions of the radioactive seeds 18 (see FIG. 1) within the prostate are determined. This ideal seed distribution is optimized to deliver a dose distribution within the prostate that will deliver all the radiation dose to the target volume only, while sparing the surrounding healthy tissues such as the rectum and bladder. The optimal positions of the seeds 18 and the optimal position of the needles 19 are recorded for later use in the operating room when the needles 19 are loaded into the patient. The seeds 18 are then loaded into the needles 19, and the physician then attempts to place the needles 19 inside the prostate according to the treatment dose plan positions (again, see example in FIG. 8).

The dose as a function of position for a cylindrical $^{125}$I seed of a given activity can be determined from a lookup table or calculated from a conventional analytic formula. The dose field can be visualized as a set of isodose lines in 2D or isodose surface in 3D. The dose computation routine is based upon the TG43 standard adopted by the AAPM (American Association of Physicists in Medicine) entitled "Dosimetry of Interstitial Brachytherapy Sources": Recommendations of the AAPM Radiation Therapy Committee Task Group No. 43 which specifies the dose model and the data used in the dose calculation. This particular implementation runs extremely fast on a conventional 233 MHz PC, computing the dose for a single seed in less than 0.5 seconds. The total 3D dose distribution within the prostate for a 100 seed implant requires only 50 seconds, or less than one minute total computation time. Thus, this can be done "on line" in the operating room.

In the 2D, 3D perspective, or the real time VR modes, the user has the ability to view the optimized seeds 18 and the needles 19 in the same volume as the real time ultrasound data. This allows the physician to see exactly where the needles 19 should go and hence make adjustments to position the needles 19 optimally. The pre-planned, optimal positioned needles 19 and the seeds 18 can be rendered again as a transparent solid, the color of which is user selectable. As the real needles 19 are inserted into the prostate, their positions relative to the ideal needle placements based on the dose plan can be monitored in real time. Any deviation of the position of a given needles 19 can be quickly and accurately readjusted so as to follow the path of the ideal needles 19. As the different needles 19 are placed at different positions inside the prostate, the viewing angle can be adjusted to facilitate viewing of the needle or catheter placement. FIGS. 5A and 5B displays perspective 3D views and the three orthogonal reconstructions of the image data along with the pre-planned catheter positions. The pre-planned needles 19 can also be viewed in the VR mode as virtual objects overlaid onto the imaging volume.

Figure 10:
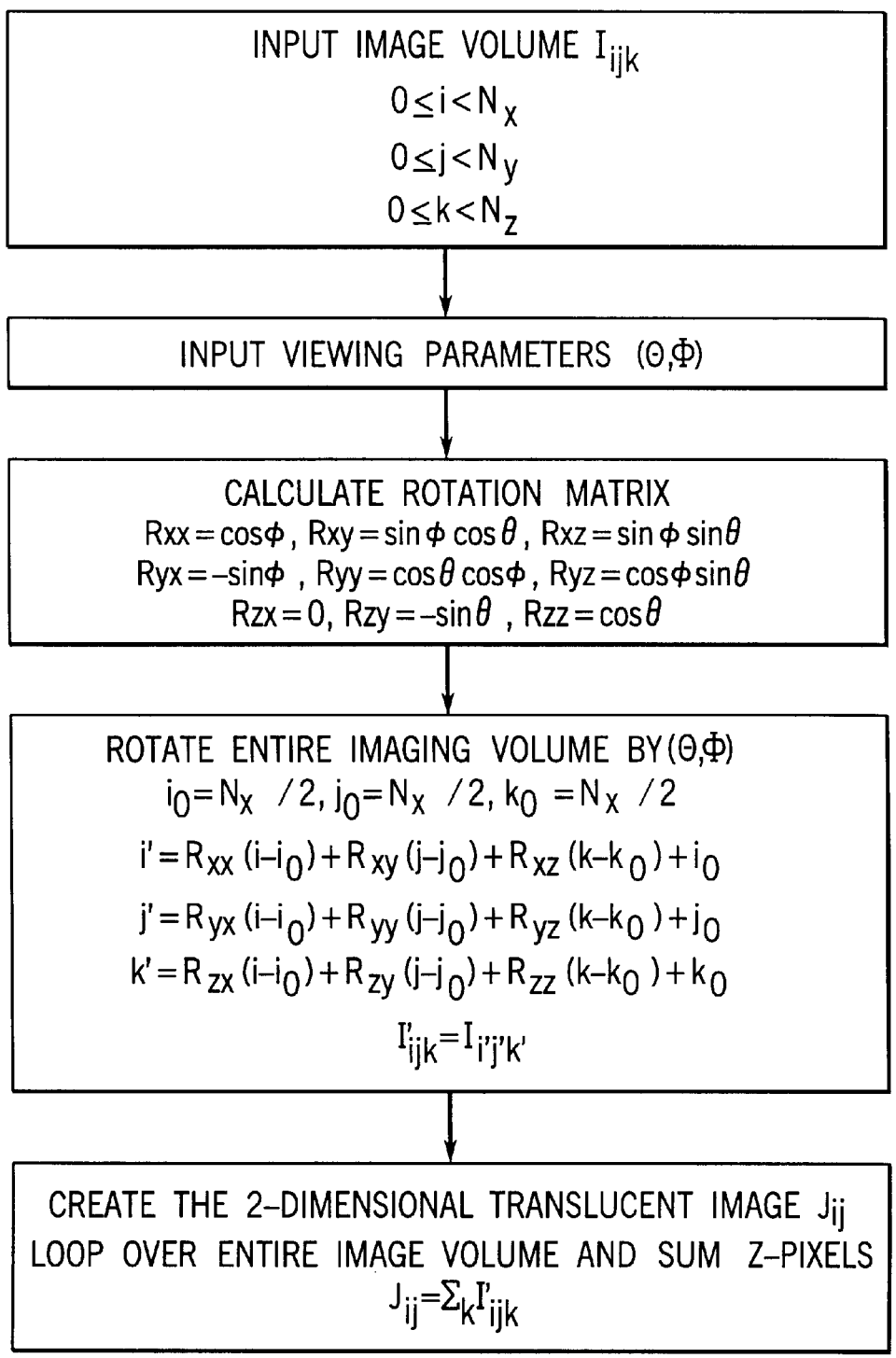
FIG. 10 illustrates a flow chart of software routine for processing imaging data for visualization.

A flowchart description of the translucent volume visualization methodology is shown in FIG. 10. The input image volume is described by the vectors i, j, k of appropriate magnitude for the volume. The viewing angle parameters are the angles θ, φ described on FIG. 6 and FIG. 10. The rotation matrix, R, is calculated using the formulae given in the flowchart of FIG. 10. The entire imaging volume is calculated by multiplying the rotation matrices in the x, y, z directions by the respective vectors i, j and k describing the incremental portions along the x, y, z directions. Thus, the multiplying vector is $(i-i_0, j-j_0, k-k_0)$ where $i_0, j_0, k_0$ are the starting points along x, y and z axes and the volume is determined by summing the component contributions shown in FIG. 10. The 3D translucent image is then created by computing the translucent 2D image over the entire image volume and summing the z-pixels.

Figure 11:
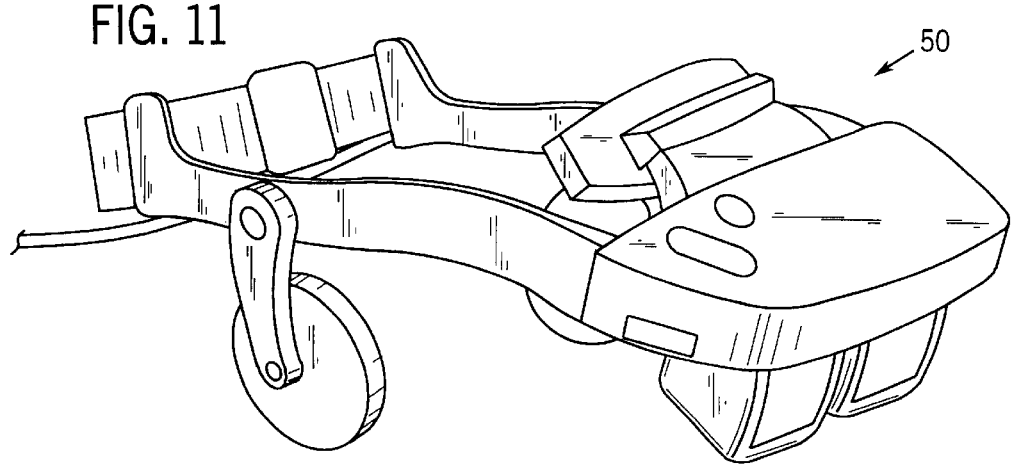
FIG. 11 illustrates a virtual reality head mounted display.

A virtual reality interface system can be composed of a conventional head mounted display (HMD) 50 shown in FIG. 11 and a 6D (x,y,z, roll, pitch, yaw) tracking system. The HMD 50 consists of two color monitors which mount to a head set in the position directly in front of the eyes. The HMD 50 is based on the principal that whatever is displayed on each monitor is directly incident on the retina for each eye, and hence true 3D images can be created by rendering objects as 3D perspective images for each eye. Given the distance between the eyes (the interoccular distance which is approximately 80 mm) and the distance and spherical angles of the distance of the center line between the eyes from the coordinate origin, the 2D images which appear in each of the two monitors can be determined exactly as described above. This results in a true 3D image as perceived by the user. Therefore, as the user moves his or her head or moves around the room, the distance from the origin and the spherical angles also change. This motion of the user or user's head can be obtained from the VR tracking system. Given these spatial parameters, the images which are reconstructed in the two eye monitors can be updated in real time, giving the user the illusion of the object really existing in 3D space. The user literally has the ability to walk around the object, viewing it in 3D space.

Instead of reconstructing computer generated geometric objects as is usually the case in VR, the transparent, 3D reconstruction of the real time imaging data will preferably be reconstructed. Hence as the physician walks around the patient undergoing the implant, the physician will see the 3D ultrasound volume mapped inside the patient's pelvis, spatially correlated to the position of the patient's real prostate (or other organ) and anatomy. The physician can "see" inside the patient to the extent of what is visible in the ultrasound imaging volume. Since the ultrasound probe 12 is locked down to the template, which is then secured to the floor, the exact positions of all voxels in the ultrasound imaging volume are known exactly relative to the template, and hence relative to the room.

As the needles 19 are inserted into the patient, they will appear in the image volume and hence are reconstructed in the VR reconstruction. All of this occurs in real time so that the physician also can see the needles 19 enter the prostate in real time. As mentioned above, if the pre-planned, optimized needles 19 are displayed, the physician can then see the position of the actual needles 19 as they are being inserted relative to the optimal placement. Hence, the physician has the ability to adjust the needles 19 to correspond to their optimal positions. In addition, since the needles 19 are automatically extracted, the computer software has the ability to calculate and render the 3D dose distribution in real time as the needles 19 are being inserted.

As an example, a currently available, a fast and inexpensive HMD is made by Virtual-IO Corporation (Mountain View, Calif.). The HMD is full color with two 0.70 LCD displays with a resolution of 180,000 pixels per LCD panel. The video input is NTSC with field sequential format. The LCD panels are semitransparent, allowing the real outside world to be included in the virtual reconstruction. The field of view is 30° for each eye. A six degree of freedom (6 DOF) tracking system can also be attached to the HMD. The 6 DOF tracking system allows for the determination of the spatial position of the user's head and the yaw, pitch, and roll of the head. The conventional head set weighs only 8 ounces and comes with stereo sound. Stereo sound is an extremely valuable technology in the operating room. With this capability, the physician has the ability to monitor the patient's heart rate and respiration rate while performing the implant. Hence any fluctuation in the patient's vital signs can be instantly accessed and acted thereon if necessary.

The radioactive seeds 18 are made of high density material such as stainless steel, and hence have a very bright response in the ultrasound images. Therefore, automatic seed detection in the ultrasound images can readily be accomplished, for example, by a simple thresholding algorithm along with the requirement that the resultant objects which are removed by threshold have a certain maximum size determined by the actual size of the seeds.

Near-real-time visualization will provide immediate feedback to the physician during the implant process itself. There is a clear need for the visualization being available during the implant process. The nearly real time visualization is of great importance to the effective use of a translucent overlay of the ideal seed pre-plan (from the therapy planning process) in the three-dimensional volume. The physician can "see" in nearly real time the relationship of the needles and seeds being implanted to the ideal pre-plan locations and quickly accommodate redirection required prior to leaving the radiation seeds. Further, the need for this in three-dimensional representation is very important to overcome the greatest fundamental limitation in brachytherapy, which is knowing at the same time both the lateral placement and longitudinal placement of needles and seeds relative to the target volume and pre-plan. This is a 3D problem which has up until now been addressed in 2D in a stepwise fashion without the ability to "see" the exact location of where you are in the target. This real time 3D visualization also would speed the implant process in the case of brachytherapy as well as make it more accurate. It would also speed other minimally invasive surgical procedures and localized tissue ablation procedures (for example, cryosurgery or localized selected ablation of diseased liver tissue or local removal of breast tissue). These procedures could be accomplished with real time visualization inside the tissue being treated with greater accuracy in shorter time. This aspect would reduce operating room time and costs to the patient and health care system.

While preferred embodiments of the inventions have been shown and described, it will be clear to those skilled in the art that various changes and modifications can be made without departing from the invention in its broader aspects as set forth in the claims provided hereinafter.

What is claimed is:

1. An apparatus for substantially real time three-dimensional imaging and treatment of the body of a patient, comprising:
   means for developing a therapy plan for treatment of an organ of the patient;
   means for providing in substantially real time image data from a treatment region of the patient's body;
   means for providing in substantially real time a translucent volume image of a portion of a patient's body and a separate translucent image of the organ of the patient; and
   means for illustrating in substantially real time a translucent therapeutic device image for placement of a therapeutic device in conjunction with the organ of the patient, wherein a simultaneous three dimensional image of the device, the organ of the patient and the portion of the patient's body is provided in substantially real time.

2. The apparatus as defined in claim 1 wherein said means for providing an image of the organ in a portion of the patient's body comprises an ultrasound probe.

3. The apparatus as defined in claim 2 wherein said ultrasound probe operates to provide a plurality of two dimensional images, thereby defining a three dimensional volume of the patient.

4. The apparatus as defined in claim 1 wherein said means for developing a therapy plan for treatment comprises a therapeutic device inserted into the organ of the patient with the device being used for delivering treatment or surgery, including at least one of radiation therapy, cryo ablation, thermal ablation and surgical resection.

5. The apparatus as defined in claim 1 wherein said means for developing a therapy plan comprises a computer configured to plan optimum treatment therapy for treatment of the organ of the patient within a portion of the patient's body.

6. The apparatus as defined in claim 5 wherein the computer is configured to define boundaries of the portion of the patient to be imaged.

7. The apparatus as defined in claim 5 wherein one or more radioactive seeds are disposed in at least one of a catheter and a needle and the computer calculates an optimum location for said radioactive seeds.

8. The apparatus as defined in claim 7 whereby said one or more radioactive seeds are positioned at a selected location by said at least one of said needle and catheter.

9. The apparatus as defined in claim 7, wherein said radioactive seeds have a selectable radiation strength.

10. The apparatus as defined in claim 1 wherein said therapeutic device comprises a catheter containing repositioned radioactive seeds.

11. The apparatus as defined in claim 1 wherein said therapeutic device comprises a surgical tool.

12. The apparatus as defined in claim 1 further including a virtual reality system for use by a clinician for observing real time treatment of the patient.

13. The apparatus as defined in claim 12 wherein said virtual reality system operates in real time and a clinician using said system can physically move around the patient and view three dimensional the portion of the patient.

14. A method of performing substantially real time three dimensional imaging and medical therapy on a patient, comprising the steps of:
   generating in substantially real time a three dimensional translucent image of a portion of a patient using a first radiation;

generating in substantially real time a three dimensional translucent image of a prostate of the patient with the image of the prostate positioned within the image of the portion of the patient, and said image of the prostate disposed within the image of the portion of the patient with a different translucent image appearance than the image of the portion of the patient;

generating in substantially real time an image of a therapeutic device being positioned within the image of the portion of the patient, the image of the therapeutic device, the prostate and the portion of the patient having a coordinated spatial reference frame; and displaying simultaneously in substantially real time the images of the portion of the patient, the prostate and the therapeutic device for real time viewing by a clinician providing therapy to the patient.

15. The method as defined in claim 14 further including the step of positioning a therapeutic device in a selected location of the portion of the patient, thereby carrying out the medical therapy on the patient.

16. The method as defined in claim 14 further including the step of developing a radiation therapy plan for treatment of the patient while performing real time imaging of the portion of the patient, and the organ of the patient.

17. The method of claim 14 farther including the step of storing 2D image data making up the three dimensional image enabling subsequent review of the 2D data.

18. The method of claim 14 wherein said images are generated from real-time 2D image data.

19. An apparatus for three-dimensional imaging and treatment of the body of a patient, comprising:

means for providing treatment of an organ of the patient;

means for providing in substantially real time image data from a treatment region of the patient's body;

means for providing in substantially real time an image of a portion of a patient's body including an image of the organ of the patient;

means for combining the image data from the treatment region with the image of the portion of the patient's body;

a spatial landmark disposed within the body of the patient for placement in conjunction with the organ of the patient, said spatial landmark being part of said means for providing treatment; and means for relating in a same coordinate space the image data from the treatment region, the image of the organ of the patient and the placement of the spatial landmark to obtain a simultaneous three-dimensional image in substantially real time of said landmark, the organ of the patient and the treatment region.

20. The apparatus as defined in claim 19 wherein said means for providing an image comprises a rapid imaging technology.

21. The apparatus as defined in claim 20 wherein said rapid imaging technology comprises at least one of an ultrasound device, a rapid CT device, and an MR device.

22. The apparatus as defined in claim 19 wherein said means for providing image data is selected from the group consisting of an ultrasound system, an MR system and a CT system.

23. The apparatus as defined in claim 19 wherein said means for providing treatment includes at least one of a catheter, a needle, a radiation source, a cryo ablation device, a thermal ablation device, a thermal therapy device, a surgical resection device and a surgical ablation device.

24. The apparatus as defined in claim 19 wherein said means for providing treatment and said spatial landmark comprises at least two radioactive seeds.

25. The apparatus as defined in claim 24 further including means for determining an ideal radioactive treatment and actual radioactive treatment for said means for providing treatment.

26. The apparatus as defined in claim 24 further including means for displaying at least one of an image of ideal radioactive treatment and actual radioactive treatment.

27. The apparatus as defined in claim 24 wherein said spatial landmark is imaged by at least one of an ultrasound device, a CT device, an MR device and a fluoroscope.

28. The apparatus as defined in claim 24 whereby said radioactive seeds are positioned at a selected location by at least one of a needle and a catheter.

29. The apparatus as defined in claim 19 further including means for imaging said spatial landmark.

30. The apparatus as defined in claim 29 wherein said means for imaging said spatial landmark comprises a rapid imaging technology.

31. The apparatus as defined in claim 30 wherein said rapid imaging technology comprises at least one of an ultrasound device, a rapid CT device, and an MR device.

32. The apparatus as defined in claim 29 wherein said means for imaging said spatial landmark in the patient's body provides a different image data set than from said image of the organ of the patient.

33. The apparatus as defined in claim 29 wherein said means for imaging said spatial landmark is selected from the imaging group of an ultrasound device, a CT device, and an MR device and said image of the organ is provided by a different one of the devices selected from the imaging group.

34. The apparatus as defined in claim 19 further including a virtual reality system for use by a clinician for observing real time imaging and treatment of the body of the patient.

35. The apparatus as defined in claim 34 wherein said virtual reality system operates in real time and a clinician using said system can physically move around the patient and view in three dimensions a portion of the patient.

36. The apparatus as defined in claim 19 further including a digitally encoded positioner and a coupled holder for retaining a treatment device, said positioner moving said treatment device into the patient and generating digital position information characteristic of spatial position in the patient, thereby establishing the spatial position of said treatment device in the patient relative to the image of the portion of the patient's body and the image of the organ.

37. The apparatus as defined in claim 36 wherein said positioner comprises a stepper device.

38. The apparatus as defined in claim 19 further including means for generating contour data for the organ of the patient.

39. The apparatus as defined in claim 19 further including means for displaying an ideal position of said means for providing treatment.

40. The apparatus as defined in claim 19 further including means for determining at least one of an ideal treatment and actual treatment for said means for treatment.

41. The apparatus as defined in claim 19 further including means for displaying at least one of an image of ideal treatment and actual treatment.

42. A method of spatially identifying a location of an internal organ of a patient for planning of radiation therapy treatment using a radiation source, comprising the steps of:

positioning a treatment device and coupled spatial marker within the patient, said spatial marker identifiable in an image of the body of the patient; and producing a first body image using a first radiation showing the internal organ and the spatial marker while maintaining said treatment device and coupled spatial marker in position within the patient, and using a second radiation different than said first radiation to generate a second body image of the spatial marker to establish a position of the treatment device relative to at least the first body image in preparation for implementing the radiation therapy treatment using the radiation source while the treatment device is in place.

43. The method as defined in claim 42 further including the step of relating a position of the internal organ to a position of the spatial marker.

44. The method as defined in claim 43 further including the step of carrying out a radiation therapy treatment by developing and implementing a radiation plan in accordance with the location of the internal organ relative to the radiation source.

45. The method as defined in claim 44 wherein the first radiation system comprises an ultrasound system and the second radiation system comprises an electromagnetic radiation system.

46. The method as defined in claim 42 wherein the first radiation includes ultrasound and the second radiation includes electromagnetic radiation.

47. The method as defined in claim 46 wherein the electromagnetic radiation arises from a device selected from the group consisting of a CT device, an MR device and a fluoroscopic device.

48. The method as defined in claim 42 wherein the first body image is related to the second body image to establish the position of the radiation therapy device.

49. The method as defined in claim 42 wherein the internal organ comprises a prostate gland.

50. A method of spatially identifying in substantially real time a location of an internal organ of a patient for radiation therapy treatment using a radiation source, comprising the steps of:

positioning a plurality of radioactive seeds within the patient, said seeds comprised of a spatial marker identifiable in images taken during planning the radiation therapy treatment;

producing a first body image using a radiation system to show the internal organ and the spatial marker;

producing a second body image using the radiation system to show body components and the spatial marker; and identifying said radioactive seeds in position prior to and during the step of performing radiation therapy with the radiation source; and correlating to a same coordinate system in substantially real time a position of the radioactive seeds to the internal organ and a position of the first body image to said second body image.

51. An apparatus for substantially real time three-dimensional imaging and treatment of the body of a patient, comprising:

a therapeutic device for providing substantially real time treatment of an organ of a patient;

means for providing substantially real time image data from a treatment region of the patient's body;

means for providing in substantially real time a translucent volume image of a volume portion of a patient's body and a separate translucent image of the organ of the patient within the volume portion of the patient; and said means for providing a translucent volume image further including means for simultaneously imaging in substantially real time a translucent image of the therapeutic device for substantially real time placement of the therapeutic device at a desired position relative to the organ of the patient, to thereby provide in substantially real time a three dimensional image of said therapeutic device during entry into and placement of the therapeutic device in association with the organ of the patient.

52. The apparatus as defined in claim 51, wherein said therapeutic device is inserted into the organ of the patient for delivering treatment or surgery, including at least one of radiation therapy, cryo ablation, thermal ablation and surgical resection.

53. The apparatus as defined in claim 51 further including means for establishing spatial position of said therapeutic device relative to the organ of the patient and a clinician viewing the image of the therapeutic device and the organ.

54. A method of performing substantially real time three dimensional imaging and medical therapy on a patient, comprising the steps of:

generating in substantially real time a three dimensional translucent image of a portion of a patient using a first radiation;

generating in substantially real time a three dimensional translucent image of an organ of the patient with the image of the organ positioned within the image of the portion of the patient, and said image of the organ disposed within the image of the portion of the patient with a different translucent image appearance than the image of the portion of the patient;

generating in substantially real time an image of a therapeutic device being positioned within the image of the portion of the patient, the image of the therapeutic device, the organ and the portion of the patient having a coordinated spatial reference frame; and displaying simultaneously in substantially real time the images of the portion of the patient, the organ and the therapeutic device for real time viewing by a clinician providing therapy to the patient.

* * * * *